US012766133B2

(12) United States Patent
Coric et al.

(10) Patent No.: US 12,766,133 B2
(45) Date of Patent: Oct. 20, 2026

(54) COMPOSITIONS AND METHODS FOR TREATING OBSESSIVE-COMPULSIVE DISORDER

(71) Applicant: Biohaven Therapeutics Ltd., New Haven, CT (US)

(72) Inventors: Vladimir Coric, Madison, CT (US); Robert Berman, New Haven, CT (US); Loren Aguiar, Lexington, MA (US)

(73) Assignee: Biohaven Therapeutics Ltd., New Haven, CT (US)

( * ) Notice: Subject to any disclaimer, the term of this patent is extended or adjusted under 35 U.S.C. 154(b) by 750 days.

(21) Appl. No.: 17/923,587

(22) PCT Filed: Jun. 24, 2021

(86) PCT No.: PCT/US2021/038789

§ 371 (c)(1),
(2) Date: Nov. 6, 2022

(87) PCT Pub. No.: WO2021/262914

PCT Pub. Date: Dec. 30, 2021

(65) Prior Publication Data

US 2023/0181541 A1 Jun. 15, 2023

Related U.S. Application Data

(60) Provisional application No. 63/043,681, filed on Jun. 24, 2020.

(51) Int. Cl.
*A61K 31/428* (2006.01)
*A61P 25/18* (2006.01)

(52) U.S. Cl.
CPC ............ *A61K 31/428* (2013.01); *A61P 25/18* (2018.01)

(58) Field of Classification Search
CPC .................................................... A61K 31/428
See application file for complete search history.

(56) References Cited

U.S. PATENT DOCUMENTS

| | | | | |
|---|---|---|---|---|
| 2018/0318288 | A1* | 11/2018 | Coric ..................... | G02B 5/285 |
| 2019/0255061 | A1 | 8/2019 | Lichenstein et al. | |
| 2019/0321317 | A1 | 10/2019 | Snodgrass et al. | |
| 2020/0085794 | A1 | 3/2020 | Wrobel et al. | |

FOREIGN PATENT DOCUMENTS

| | | | | | |
|---|---|---|---|---|---|
| CA | 3082096 | | 5/2019 | | |
| WO | 2019231865 | A1 | 12/2019 | | |
| WO | 2020023324 | | 1/2020 | | |
| WO | WO-2020037152 | A1 * | 2/2020 | ............. | A61P 25/22 |

OTHER PUBLICATIONS

NCT03299166, Troriluzole (BHV-4157) in Adult Participants With Obsessive Compulsive Disorder, update from Jun. 4, 2020, available at https://clinicaltrials.gov/study/NCT03299166?cond=Obsessive-Compulsive%20Disorder&intr=Troriluzole%20%5C(BHV-4157%5C)&rank=2&tab=history&a=63#version-content-panel.*

Wiah, Troriluzole inhibits methamphetamine place preference in rats and normalizes methamphetamine-evoked glutamate carboxypeptidase II (GCPII) protein levels in the mesolimbic pathway, Drug Alcohol Depend. Author manuscript; available in PMC: Jan. 1, 2024.*

Troriluzole (also known as Trigriluzole, BHV-4157, and FC-4157), published by Cognitive Vitality Reports® at Cognitive Vitality.org, last updated on Feb. 26, 2020, available at https://www.alzdiscovery.org/uploads/cognitive_vitality_media/Troriluzole-Cognitive-Vitality-For-Researchers.pdf.*

International Search Report dated Oct. 6, 2021 issued for International Application No. PCT/US2021/038789 (2 pages).

Written Opinion dated Oct. 6, 2021 issued for International Application No. PCT/US2021/038789 (6 pages).

International Preliminary Report on Patentability dated Dec. 13, 2022 issued for International Application No. PCT/US2021/038789 (7 pages).

"Biohaven Announces Obsessive-Compulsive Disorder (OCD) Proof of Concept Phase 2/3 Study Results and Program"—press-release article published on Jun. 24, 2020 at https://www.prnewswire.com/news-releases/biohaven-announces-obsessive-compulsive-disorder-ocd-proof-of-concept-phase-23-study-results-and-program-update-301082586.html.

Sartori, Simone B. et al: "Novel pharmacological targets in drug development for the treatment of anxiety and anxiety-related disorders", Pharmacology & Therapeutics, Elsevier, GB, vol. 204, Aug. 27, 2019.

Pittenger, Christopher, et al: "Riluzole augmentation in treatement-refractory obsessive-compulsive disorder: a pilot placebo-controlled trial", J Clin Psychiatry, Aug. 2015, 76(8): 1075-1084.

J.N. De Boer et al., "Efficacy and tolerability of riluzole in psychiatric disorders: A systematic review and preliminary meta-analysis", Psychiatry Research , Aug. 2019, vol. 278 , p. 294-302 , DOI: 10.1016/j.psychres.2019.06.020.

Somaye Arabzadeh et al., "L-carnosine as an adjuvant to fluvoxamine in treatment of obsessive compulsive disorder: A randomized double-blind study", Human Psychopharmacology: Clinical and Experimental, May 8, 2017, vol. 32, No. 4, p. e2584, DOI: 10.1002/hup.258.

Partial English Translation of Mitsuhiko Yamada et al., Development of new drug therapies controlling the processing of fear memories, Japanese Journal of Biological Psychiatry, 2018, vol. 29, No. 2, p. 60-63.

Extended European Search Report dated Jul. 3, 2024 in corresponding European Application No. 21829059.3.

Notice of Deficiencies dated Dec. 14, 2025 in corresponding Israeli Application No. 299301.

* cited by examiner

*Primary Examiner* — Svetlana M Ivanova
(74) *Attorney, Agent, or Firm* — Stites & Harbison, PLLC

(57) ABSTRACT

Disclosed herein is a method for treating obsessive-compulsive disorder in a patient in need thereof by administering to the patient a dosage form including an effective amount of troriluzole.

17 Claims, 2 Drawing Sheets

| | | | | |
|---|---|---|---|---|
| Troriluzole | N=113 | N=111 | N=96 | N=99 |
| Placebo | N=117 | N=113 | N=108 | N=102 |

Mean Y-BOCS Total scores measured at Baseline and Weeks 4, 8, and 12 (observed case analysis) during treatment with Troriluzole or placebo in the modified intent-to-treat population. Post-baseline p value is for change from baseline. ★ p≤0.05.

COMPOSITIONS AND METHODS FOR TREATING OBSESSIVE-COMPULSIVE DISORDER

CROSS-REFERENCE TO RELATED APPLICATIONS

This application is a national stage application under 35 U.S.C. § 371 of Internation Application No. PCT/US2021/038789, fled Jun. 24, 2021, which claims priority to U.S. Provisional Application No. 63/043,681 filed Jun. 24, 2020 and all the benefits accruing therefrom under 35 U.S.C. § 119, the content of which is incorporated herein in its entirety by reference.

FIELD OF THE INVENTION

The present invention relates to pharmaceutical compositions for treating obsessive-compulsive disorder (OCD) with riluzole prodrugs. Specifically, the present invention relates to methods of treating OCD with pharmaceutical compositions containing troriluzole.

BACKGROUND OF THE INVENTION

Obsessive Compulsive Disorder ("OCD") is a debilitating psychiatric condition, which is characterized by recurrent, intrusive thoughts (obsessions) and/or repetitive, stereotyped behaviors (compulsions) that last for at least one hour per day and significantly interfere with an individual's normal level of functioning. Although cognitive behavioral therapy and pharmacotherapy with selective serotonin reuptake inhibitors (SSRI) are effective treatments for some patients, a substantial subset experience minimal relief from their symptoms with these standard treatments. When severe, OCD is completely incapacitating with devastating consequences for patients and their families. Augmentation strategies with neuroleptic medications can improve the effectiveness of SSRI therapy, but do not eliminate OCD symptoms (Saxena et al., J. Clin. Psychiatry, 1996, 57, 303-306, 1996; McDougle et al., J. Clin. Psychiatry, 1995, 56, 526-528) and are associated with adverse effects, when used chronically. The clinical observation that few patients experience a complete response to SSRI or dopamine antagonists suggests that other neurochemical systems are involved in the pathophysiology of OCD.

OCD affects one person in 40 and over 2 million individuals in the United States, significantly affecting quality of life. A third of patients do not respond to current treatments. Approximately 40% to 60% of OCD patients continue to experience significant residual symptoms despite approved therapies. Some refractory patients undergo psychosurgery (cingulotomy or deep brain stimulation) to alleviate their crippling symptoms.

There has not been a mechanistically novel medication approved for OCD in over 20 years. Therefore, new therapies are urgently needed to alleviate the suffering and disability of OCD patients.

SUMMARY OF THE INVENTION

The present invention is directed to a pharmaceutical composition including troriluzole and methods for treating obsessive-compulsive disorder using the composition.

In an embodiment, a method for treating obsessive-compulsive disorder in a patient in need thereof is provided. The method includes administering to the patient a dosage form including an effective amount of troriluzole.

In another embodiment, a dosage form including troriluzole in an amount effective to treat obsessive-compulsive disorder in a patient in need thereof is provided.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION OF THE INVENTION

Figure 1:
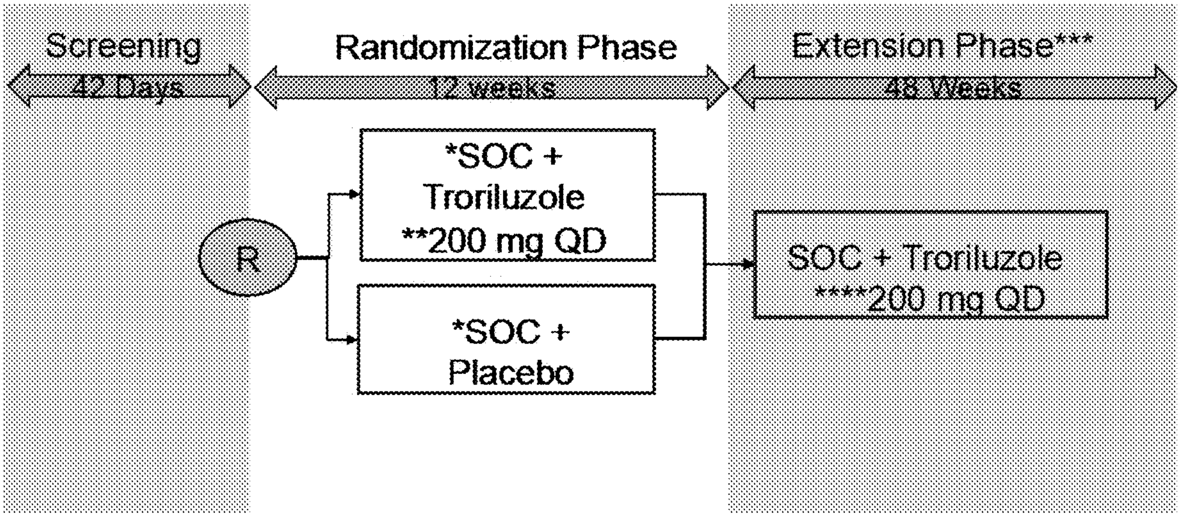
FIG. 1 shows troriluzole OCD Phase ⅔ study design.
Figure 2:
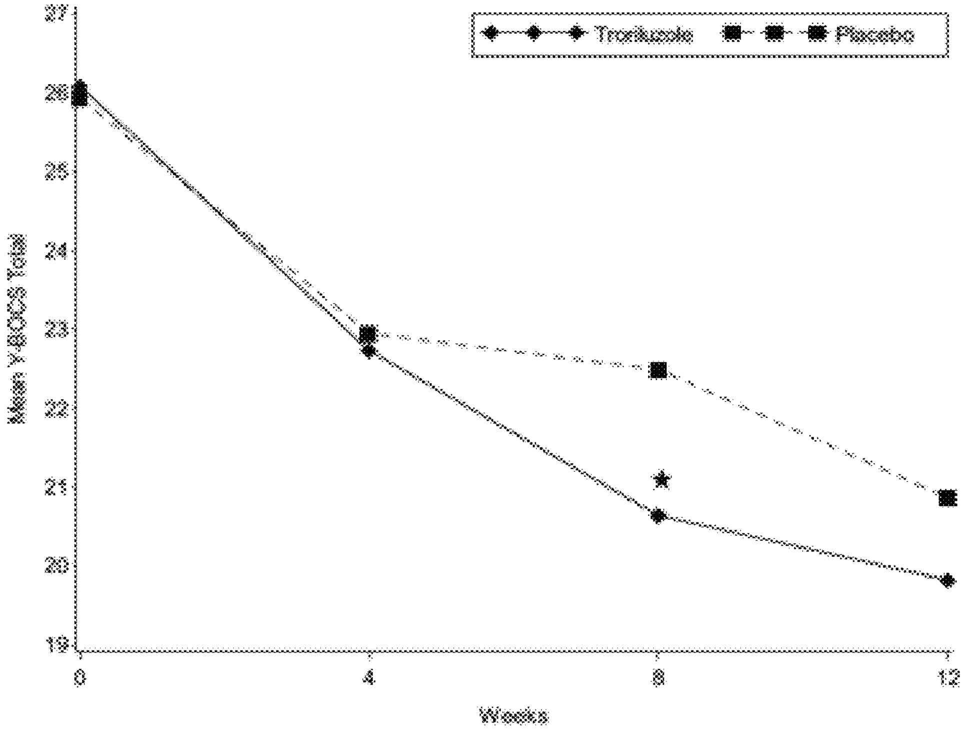
FIG. 2 shows troriluzole study mean Y-BOCS scores at baseline and Weeks 4, 8, and 12.

The following detailed description is provided to aid those skilled in the art in practicing embodiments of the present invention. Exemplary embodiments will hereinafter be described in detail. However, these embodiments are only exemplary, and the present disclosure is not limited thereto but rather is defined by the scope of the appended claims. Those of ordinary skill in the art may make modifications and variations in the embodiments described herein without departing from the spirit or scope of the present disclosure.

Accordingly, the embodiments are merely described below, by referring to structures and schemes, to explain aspects of the present description. As used herein, the term "and/or" includes any and all combinations of one or more of the associated listed items. The term "or" means "and/or." Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

It is understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all technical and scientific terms used herein have the same meaning as commonly understood by one of ordinary skill in the art to which this disclosure belongs. The terminology used in the description is for describing particular embodiments only and is not intended to be limiting. It will be further understood that the terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used in this application, except as otherwise expressly provided herein, each of the following terms shall have the meaning set forth below. Additional definitions are set forth throughout the application. In instances where a term is not specifically defined herein, that term is given an art-recognized meaning by those of ordinary skill applying that term in context to its use in describing embodiments of the present invention.

The articles "a" and "an" refer to one or to more than one (i.e., to at least one) of the grammatical object of the article unless the context clearly indicates otherwise. By way of example, "an element" means one element or more than one element.

Additional aspects will be set forth in part in the description which follows and, in part, will be apparent from the description.

Obsessive-Compulsive Disorder

The methods and compositions, according to embodiment of the present invention, are useful in the treatment of obsessive-compulsive disorder ("OCD"). In some embodiments of the invention, the individual treated according to the claimed method is assessed using the Yale Brown Obsessive Compulsive Scale ("Y-BOCS"). See Goodman et al., Arch. Gen. Psychiatry, 1989, 46, 1006-1011. According to this system, an individual is scored using a symptom checklist by asking the individual about specific obsessions and compulsions. Such symptoms are broadly categorized as aggressive obsessions, contamination obsessions, sexual obsessions, hoarding/saving obsessions, religious obsessions, obsession with need for symmetry or exactness, miscellaneous obsessions, somatic obsessions, cleaning/washing compulsions, checking compulsions, repeating rituals, counting compulsions, ordering/arranging compulsions, and miscellaneous compulsions. Each of these categories is further divided by subcategory of more specific symptoms. Individuals are scored according to the answers provided. Scores range from 0-7 for subclinical, 8-15 for mild, 16-23 for moderate, 24-31 for severe, and 32-40 for extreme severity. In some embodiments of the invention, the individual displays a Yale Brown Obsessive Compulsive Scale score of at least 20 prior to treatment. In other embodiments, the individual displays a score of at least 24, at least 26, at least 28, at least 30, at least 32, at least 34, or at least 36 prior to treatment.

According to the Y-BOCS system, the broad symptom categories may be further subdivided. Subcategories of aggressive obsessions include: fear might harm self; fear might harm others; violent or horrific images; fear of blurting out obscenities or insults; fear of doing something else embarrassing; fear will act on unwanted impulses (e.g., to stab friend); fear will steal things; fear will harm others because not careful enough; (e.g., hit/run motor vehicle accident); and fear will be responsible for something else terrible happening (e.g., fire, burglary). Subcategories of contamination obsessions include: concerns or disgust w\with bodily waste or secretions (e.g., urine, feces, saliva), concern with dirt or germs; excessive concern with environmental contaminants (e.g. asbestos, radiation toxic waste); excessive concern with household items (e.g., cleansers solvents); excessive concern with animals (e.g., insects); bothered by sticky substances or residues; concerned will get ill because of contaminant; concerned will get others ill by spreading contaminant (aggressive); and no concern with consequences of contamination other than how it might feel. Subcategories of sexual obsessions include: forbidden or perverse sexual thoughts, images, or impulses; content involves children or incest; content involves homosexuality; and sexual behavior towards others (aggressive). Subcategories of religious obsessions include: concerned with sacrilege and blasphemy; and excess concern with right/wrong, morality. Subcategories of obsession with need for symmetry of exactness include: accompanied by magical thinking (e.g., concerned that another will have accident dent unless things are in the right place); and not accompanied by magical thinking. Subcategories of miscellaneous obsessions include: need to know or remember; fear of saying certain things; fear of not saying just the right thing; fear of losing things; intrusive (nonviolent) images; intrusive nonsense sounds, words, or music; bothered by certain sounds/noises; lucky/unlucky numbers; colors with special significance; and 3 superstitious fears.

Subcategories of somatic obsessions include: concern with illness or disease; and excessive concern with body part or aspect of appearance (e.g., dysmorphophobia). Subcategories of cleaning/washing compulsions include: excessive or ritualized handwashing; excessive or ritualized showering, bathing, toothbrushing grooming, or toilet routine, involves cleaning of household items or other inanimate objects; and other measures to prevent or remove contact with contaminants. Subcategories of checking compulsions include: checking locks, stove, appliances etc.; checking that did rot/will not harm others; checking that did not/will not harm self; checking that nothing terrible did/will happen; checking that did not make mistake; and checking tied to somatic obsessions. Subcategories of repeating rituals include: rereading or rewriting; and need to repeat routine activities (jog, in/out door, up/down from chair). Subcategories of miscellaneous compulsions include: mental rituals (other than checking/counting); excessive list-making; need to tell, ask, or confess; need to touch, tap, or rub; rituals involving blinking or staring; measures (not checking) to prevent: harm to self-harm to others terrible consequences; ritualized eating behaviors; superstitious behaviors; Trichotillomania; other self-damaging or self-mutilating behaviors.

Troriluzole

Troriluzole (BHV-4157) is a third-generation prodrug and new chemical entity that modulates glutamate, the most abundant excitatory neurotransmitter in the human body. The primary mode of action of troriluzole is reducing synaptic levels of glutamate. Troriluzole increases glutamate uptake from the synapse, by augmenting the expression and function of excitatory amino acid transporters (i.e., EAAT2) located on glial cells that play a key role in clearing glutamate from the synapse. Glutamatergic dysfunction is implicated in the pathophysiology of a broad range of disorders including Amyotrophic Lateral Sclerosis (ALS), Spinocerebellar Ataxia (SCA), Alzheimer's Disease (AD), generalized anxiety disorder, depression, obsessive compulsive disorder (OCD), post-traumatic stress disorder (PTSD), chronic pain, and a variety of cancers. The therapeutic potential of troriluzole is supported by clinical and translational research studies conducted with riluzole in a variety of these indications. Troriluzole is described, for example, in U.S. Pat. No. 10,485,791.

Administration and Dosage

The methods and compositions, according to embodiments of the present invention are used to treat a patient having an obsessive-compulsive disorder. As used herein, the term "treating" refers to the lessening or alleviation of symptoms of a particular disorder in an individual or the improvement of an ascertainable measurement associated with a particular disorder, for example OCD.

In an aspect, embodiments of the invention provides a pharmaceutical composition in the form of a dosage form that includes troriluzole in an amount effective to treat obsessive-compulsive disorder in a patient in need thereof. The amount of troriluzole in the dosage form may be 200 mg or greater, for example, 250 mg or greater, 300 mg or greater, 350 mg or greater, 400 mg or greater, 450 mg or greater, or 500 mg or greater.

The dosage form may further include a pharmaceutically acceptable excipient. As used herein, the term "pharmaceutically acceptable excipient" refers to an excipient that may be administered to a patient, together with troriluzole, and which does not destroy the pharmacological activity of troriluzole and is non-toxic when administered in doses sufficient to deliver a therapeutic amount of troriluzole.

Pharmaceutically acceptable excipients that may be used in the pharmaceutical compositions, according to embodiments of the present invention, include, but are not limited to, ion exchangers, alumina, aluminum stearate, lecithin, self-emulsifying drug delivery systems (SEDDS) such as α-tocopherol, polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl cyclodextrins, or other solubilized derivatives may also be advantageously used to enhance delivery of troriluzole.

The pharmaceutical compositions, according to embodiments of the present invention, may be administered orally, parenterally, by inhalation spray, topically, rectally, nasally, buccally, vaginally or via an implanted reservoir. The pharmaceutical compositions, according to embodiments of the present invention, may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated troriluzole or its delivery form. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions disclosed herein may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as those described in Pharmacopeia Helvetica or a similar alcohol, or carboxymethyl cellulose or similar dispersing agents which are commonly used in the formulation of pharmaceutically acceptable dosage forms such as emulsions and/or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions, according to embodiment of the present invention, may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions disclosed herein may also be administered in the form of suppositories for rectal administration. These compositions can be prepared by mixing troriluzole with a suitable non-irritating excipient which is solid at room temperature but liquid at the rectal temperature, and therefore, will melt in the rectum to release the active components. Such materials include, but are not limited to, cocoa butter, beeswax and polyethylene glycols.

Topical administration of the pharmaceutical compositions, according to embodiments of the present invention, is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of troriluzole include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing troriluzole suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions, according to embodiment of the present invention, may also be topically applied to the lower intestinal tract by rectal suppository formulation or in a suitable enema formulation. Topically-transdermal patches are also included in this invention.

The pharmaceutical compositions, according to embodiments of the invention, may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The pharmaceutical compositions, according to embodiments of the present invention, may conveniently be presented in unit dosage form and may be prepared by any methods well known in the art of pharmacy. The amount of active ingredient that can be combined with a carrier material to produce a single dosage form will vary depending upon the host being treated, the particular mode of administration. The amount of active ingredient that can be combined with a carrier material to produce a single dosage form will generally be that amount of troriluzole that produces a therapeutic effect. Generally, out of one hundred percent, this amount will range in some embodiments from about 1 percent to about ninety-nine percent of active ingredient, in some embodiments from about 5 percent to about 70 percent, and in some embodiments from about 10 percent to about 30 percent.

The selected dosage level will depend upon a variety of factors including the activity of troriluzole, or the ester, salt or amide thereof, the route of administration, the time of administration, the rate of excretion of troriluzole, the duration of the treatment, other drugs, compounds and/or materials used in combination with the particular compound employed, the age, gender, weight, condition, general health and prior medical history of the patient being treated, and like factors well known in the medical arts.

A physician having ordinary skill in the art can readily determine and prescribe the effective amount of the pharmaceutical composition required. For example, the physician could start doses of troriluzole employed in the pharmaceutical composition at levels lower than that required in order to achieve the desired therapeutic effect and gradually increase the dosage until the desired effect is achieved.

In general, a suitable daily dose of troriluzole will be that amount that is the lowest dose effective to produce a therapeutic effect. Such an effective dose will generally depend upon the factors described above.

If desired, the effective daily dose of troriluzole may be administered as one, two, three, four, five, six or more sub-doses administered separately at appropriate intervals throughout the day, optionally, in unit dosage forms. In certain embodiments of the present invention, troriluzole may be administered two or three times daily. In some embodiments, troriluzole will be administered once daily.

In another aspect of the invention, troriluzole is administered alone or co-administered with another therapeutic agent. As used herein, the phrase "co-administration" refers to any form of administration of two or more different therapeutic compounds such that the desired effect is obtained. For example, the second compound is administered while the previously administered therapeutic compound is still effective in the body (e.g., the two compounds are simultaneously effective in the patient, which may include synergistic effects of the two compounds). The different therapeutic compounds may be administered either in the same formulation or in a separate formulation, either concomitantly or sequentially. Thus, an individual who receives such treatment may benefit from a combined effect of different therapeutic compounds. Co-administration includes simultaneous or sequential administration of two or more compounds.

In certain embodiments, troriluzole is co-administered with a serotonin reuptake inhibitor. The serotonin reuptake inhibitor is, for example, citalopram, escitalopram, flouxetine, fluvoxamine, paroxetine, sertraline, trazodone, venlafaxine, mirtazepine, clomipramine, or combinations with other psychotropic medications including an anti-psychotic, an anti-convulsant, a tricyclic antidepressant, a monoamine oxidase inhibitor, a selective serotonin reuptake inhibitor, a selective serotonin-norepinephrine reuptake inhibitor, a norepinephrine dopamine reuptake inhibitor, a serotonin-2 antagonist reuptake inhibitor, a benzodiazepine, a wakefulness promoting agent, anti-manic agent, or a combination of one or more of the foregoing.

In another embodiment, a method for treating obsessive-compulsive disorder in a patient in need thereof is provided. The method includes administering to the patient a dosage form including an effective amount of troriluzole.

The dosage form may be administered daily for four weeks or longer, and the patient at week 4 may have a mean Y-BOCS total scale change of at least −3.4 points from baseline. The dosage form may be administered daily for four weeks or longer, and the patient at week 4 may have a mean Y-BOCS total scale change of at least 0.5 points compared to placebo.

The dosage form may be administered daily for eight weeks or longer, and at week 8 the patient may have a mean Y-BOCS total scale change of at least −5.1 points from baseline. The dosage form may be administered daily for eight weeks or longer, and the patient at week 8 may have a mean Y-BOCS total scale change of at least 1.5 points compared to placebo.

The dosage form may be administered daily for twelve weeks or longer, and at week 12 the patient may have a mean Y-BOCS total scale change of −5.9 points from baseline. The dosage form may be administered daily for twelve weeks or longer, and the patient at week 12 may have a mean Y-BOCS total scale change of 1.0 points compared to placebo.

The patient has a median Y-BOCS score of 26 or greater. The dosage form may be administered daily for four weeks or longer, and the patient at week 4 may have a mean Y-BOCS total scale change of at least −4.1 points from baseline. The dosage form may be administered daily for four weeks or longer, and the patient at week 4 may have a mean Y-BOCS total scale change of at least 0.6 points compared to placebo.

The dosage form may be administered daily for eight weeks or longer, and at week 8 the patient may have a mean Y-BOCS total scale change of at least −6.0 points from baseline. The dosage form may be administered daily for eight weeks or longer, and the patient at week 8 may have a mean Y-BOCS total scale change of at least 2.9 points compared to placebo.

The dosage form may be administered daily for twelve weeks or longer, and at week 12 the patient may have a mean Y-BOCS total scale change of −7.0 points from baseline. The dosage form is administered daily for twelve weeks or longer, and the patient at week 12 may have a mean Y-BOCS total scale change of 2.4 points compared to placebo.

The invention is further illustrated by the following non-limiting examples.

Example: Troriluzole Proof of Concept Obsessive-Compulsive Disorder (OCD) Study

Study Design

The study design is schematically shown in FIG. 1. Subjects are taking the maximum tolerated dose of a selective serotonin reuptake inhibitor (SSRI) or clomipramine for at least 10 weeks at Baseline*. Subjects receive a dose of 140 mg QD for the first four (4) weeks, and the dose is then increased to 200 mg QD for the duration of the study. Down titration is only allowed to address tolerability issues. Eligible subjects include those who perceived benefit in earlier phases or for whom the Principal Investigator (PI) believes extended treatment with BHV-4157 would offer an acceptable risk-benefit profile*. Subjects start the Extension phase on the dose that was taken at the end of the Randomization phase. Subjects receiving placebo in the randomization phase are blindly switched to a 140 mg dose QD for the first 4 week, and the dose is then increased to 200 mg QD (at the Week 4 visits). Down titration is only allowed to address tolerability issues. All visits after Week 4 are open-label****.

Subjects who are stable on Standard of Care (SOC) medication and having an inadequate response to SOC are randomized to additionally receive placebo (QD) or troriluzole for 12 weeks (200 mg QD, after four weeks at 140 mg QD). Subjects completing the Randomization Phase are offered approximately 48 weeks of open-label treatment. The study is conducted from December 2017 to June 2020 with 242 subjects randomized at over 56 sites. The full study details are available online at https://clinicaltrials.gov/ct2/show/study/NCT03299166?term=biohaven&cond=Obsessive-Compulsive+Disorder&draw=2&rank=1.

Key Inclusion Criteria

The study involves subjects with a primary diagnosis of OCD as per Diagnostic and Statistical Manual of Mental Disorders, Fifth Edition, as confirmed by the MINI at screening.

Duration of the subject's illness must be equal to or greater than 1 year.

The subjects must be currently experiencing non-response or inadequate response to their current Standard of Care (SOC) medication defined as: (1) subjects Y-BOCS total score must be equal to or greater than 19 at screening and baseline, reflecting moderate or severe OCD symptoms; and (2) the subjects must currently be on a selective serotonin reuptake inhibitor (SSRI) or clomipramine, venlafaxine or desvenlafaxine monotherapy treatment for an adequate duration (at least 8 weeks at screening and 10 weeks at baseline) and at an adequate dose.

The Clinical Global Impression Score (CGI-S) must be equal to or greater than 4 at screening and baseline.

Key Exclusion Criteria

Subjects are excluded with a history of more than two (2) previous failed treatment trials of SSRIs, clomipramine, venlafaxine, or desvenlafaxine, (not including the current SSRI trial) given for an adequate duration at an adequate dose as defined by the MGH-TRQ-OCD.

Subjects are excluded if they display acute suicidality or suicide attempt or self-injurious behavior in the last 12 months.

Subjects are excluded if they have a Brown Assessment of Beliefs (BABS) score of greater than 17 at screening and baseline.

Use of a stimulant, neuroleptic (antipsychotic), mood stabilizer and glutamate agent (e.g., topiramate, lamotrigine, N-acetylcysteine, ketamine, memantine, sodium valproate) is prohibited within the 4 weeks prior to screening and during the study.

Current daily anxiolytic or benzodiazepine use is prohibited.

Study Results

The results of the primary endpoint analysis are listed in Tables 1 to 5 below:

TABLE 1

BHV4157-202 Final Unblinded Analysis
YBOCS Total Change from Baseline by Week
LSMeans and SE from MMRM Model
MITT Data Set

| | Placebo | | Troriluzole | | Troriluzole vs Placebo | | |
|---|---|---|---|---|---|---|---|
| | | LS | | LS | Difference | | |
| Week | N | Mean | N | Mean | Estimate | 95% CI | p-value |
| 4 | 115 | −2.9 | 111 | −3.4 | −0.5 | (−1.67, 0.75) | 0.451 |
| 8 | 108 | −3.6 | 96 | −5.1 | −1.5 | (−3.02, −0.06) | 0.041 |
| 12 | 102 | −4.9 | 99 | −5.9 | −1.0 | (−2.59, 0.60) | 0.220 |

Table 1 shows the mean change in the Yale-Brown Obsessive-Compulsive Scale (Y-BOCS) total score over time. Troriluzole treated subjects had a mean Y-BOCS improvement of −5.1 points from baseline versus −3.6 for placebo-treated subjects [difference −1.5, p-value=0.041, 95% CI:−3.02, −0.06] at week 8, and −5.9 points versus −4.9 for placebo subjects [difference −1.0, p-value=0.220, 95% CI:−2.59, 0.60] at week 12. Although the p-value in this proof of concept study did not reach statistical significance at the primary Y-BOCS endpoint at week 12, the results reveal a consistent treatment benefit of troriluzole over time and provide the appropriate data to power future studies. The plotted results are shown in FIG. 1.

TABLE 2

BHV4157-202 Final Unblinded Analysis
YBOCS Obsessions Subscale Change from Baseline by Week
LSMeans and SE from MMRM Model
MITT Data Set

| | Placebo | | Troriluzole | | Troriluzole vs Placebo | | |
|---|---|---|---|---|---|---|---|
| | | LS | | LS | Difference | | |
| Week | N | Mean | N | Mean | Estimate | 95% CI | p-value |
| 4 | 115 | −1.65 | 111 | −1.67 | −0.02 | (−0.70, 0.66) | 0.952 |
| 8 | 108 | −2.15 | 96 | −2.50 | −0.36 | (−1.23, 0.51) | 0.419 |
| 12 | 102 | −2.55 | 99 | −2.91 | −0.36 | (−1.24, 0.52) | 0.422 |

TABLE 3

BHV4157-202 Final Unblinded Analysis
YBOCS Compulsions Subscale Change from Baseline by Week
LSMeans and SE from MMRM Model
MITT Data Set

| | Placebo | | Troriluzole | | Troriluzole vs Placebo | | |
|---|---|---|---|---|---|---|---|
| | | LS | | LS | Difference | | |
| Week | N | Mean | N | Mean | Estimate | 95% CI | p-value |
| 4 | 115 | −1.28 | 111 | −1.72 | −0.44 | (−1.09, 0.22) | 0.194 |
| 8 | 108 | −1.41 | 96 | −2.61 | −1.20 | (−1.98, −0.43) | 0.003 |
| 12 | 102 | −2.37 | 99 | −3.01 | −0.64 | (−1.50, 0.22) | 0.143 |

TABLE 4

BHV4157-202 Final Unblinded Analysis
YBOCS Total Change from Baseline by Week
LSMeans and SE from MMRM Model
MITT Data Set
Only Subjects > Baseline YBOCS = 26 (Median)

| | Placebo | | Troriluzole | | Troriluzole vs Placebo | | |
|---|---|---|---|---|---|---|---|
| | | LS | | LS | Difference | | |
| Week | N | Mean | N | Mean | Estimate | 95% CI | p-value |
| 4 | 47 | −3.5 | 49 | −4.1 | −0.6 | (−2.80, 1.58) | 0.584 |
| 8 | 45 | −3.1 | 42 | −6.0 | −2.9 | (−5.49, −0.21) | 0.035 |
| 12 | 43 | −4.6 | 44 | −7.0 | −2.4 | (−5.18, 0.33) | 0.084 |

Troriluzole treatment differences compared to placebo were greater in patients who were more severely ill at baseline (i.e., Y-BOCs total scores greater than the median score of 26, representing severe OCD symptoms), see Table 2. Troriluzole treated subjects (n=42) had a mean Y-BOCS change from baseline of −6.0 points versus −3.1 for placebo (n=45) subjects [difference −2.9, p=0.035, 95% CI:−5.49, −0.21] at week 8, and −7.0 points (n=44) versus −4.6 for placebo (n=43) subjects [treatment difference −2.4, p=0.084, 95% CI:−5.18, 0.33] at week 12.

TABLE 5

BHV4157-202 Final Unblinded Analysis (Not Validated)
YBOCS Total Score Change from Baseline by Week
LSMeans and SE from MMRM Model
MITT Data Set
Only Subjects <= Median Baseline YBOCS Total = 26

| | Placebo | | Troriluzole | | |
|---|---|---|---|---|---|
| Week | N | LS Mean | N | LS Mean | p-value |
| 4 | 68 | −2.6 | 62 | −2.8 | 0.783 |
| 8 | 63 | −4.0 | 54 | −4.4 | 0.617 |
| 12 | 59 | −5.2 | 55 | −5.0 | 0.877 |

Summary of Topline Results

Troriluzole 200 mg administered once daily as adjunctive therapy in OCD patients with inadequate response to standard of care treatment showed consistent numerical improvement over placebo on the Yale-Brown Obsessive Compulsive Scale (Y-BOCS) at all study timepoints (weeks 4 to 12) but did not meet the primary outcome measure at week 12, p<0.05 at week 8 and p=0.22 at week 12. Strong signal is observed in compulsive behaviors and in patients with severe disease, as evidenced by the Y-BOCS compulsion subscale changes. Troriluzole safety profile is safe and well tolerated, and appears to be consistent with other troriluzole trials. The trial is considered Proof of Concept study for troriluzole as adjunctive therapy in OCD patients with inadequate response to standard of care treatment.

Throughout this application, various publications are referenced by author name and date, or by patent number or patent publication number. The disclosures of these publications are hereby incorporated in their entireties by reference into this application in order to more fully describe the state of the art as known to those skilled therein as of the date of the invention described and claimed herein. However, the citation of a reference herein should not be construed as an acknowledgement that such reference is prior art to the present invention.

Those skilled in the art will recognize, or be able to ascertain using no more than routine experimentation, numerous equivalents to the specific procedures described herein. Such equivalents are considered to be within the scope of this invention and are covered by the following claims. For example, pharmaceutically acceptable salts other than those specifically disclosed in the description and Examples herein can be employed. Furthermore, it is intended that specific items within lists of items, or subset groups of items within larger groups of items, can be combined with other specific items, subset groups of items or larger groups of items whether or not there is a specific disclosure herein identifying such a combination.

The invention claimed is:

1. A method for treating obsessive-compulsive disorder in a patient in need thereof, comprising orally administering to the patient a dosage form comprising troriluzole in an amount of 200 mg or greater, wherein the patient has a median Y-BOCS score of 26 or greater, and wherein the troriluzole is co-administered with a selective serotonin reuptake inhibitor, clomipramine, venlafaxine, or desvenlafaxine.

2. The method of claim 1, wherein the dosage form is administered daily for four weeks or longer, and wherein the patient at week 4 has a mean Y-BOCS total scale change of at least-3.4 points from baseline.

3. The method of claim 1, wherein the dosage form is administered daily for four weeks or longer, and wherein the patient at week 4 has a mean Y-BOCS total scale change of at least 0.5 points compared to placebo.

4. The method of claim 1, wherein the dosage form is administered daily for eight weeks or longer, and wherein at week 8 the patient has a mean Y-BOCS total scale change of at least-5.1 points from baseline.

5. The method of claim 1, wherein the dosage form is administered daily for eight weeks or longer, and wherein the patient at week 8 has a mean Y-BOCS total scale change of at least 1.5 points compared to placebo.

6. The method of claim 1, wherein the dosage form is administered daily for twelve weeks or longer, and wherein at week 12 the patient has a mean Y-BOCS total scale change of −5.9 points from baseline.

7. The method of claim 1, wherein the dosage form is administered daily for twelve weeks or longer, and wherein the patient at week 12 has a mean Y-BOCS total scale change of 1.0 points compared to placebo.

8. The method of claim 1, wherein the dosage form is administered daily for four weeks or longer, and wherein the patient at week 4 has a mean Y-BOCS total scale change of at least-4.1 points from baseline.

9. The method of claim 1, wherein the dosage form is administered daily for four weeks or longer, and wherein the patient at week 4 has a mean Y-BOCS total scale change of at least 0.6 points compared to placebo.

10. The method of claim 1, wherein the dosage form is administered daily for eight weeks or longer, and wherein at week 8 the patient has a mean Y-BOCS total scale change of at least-6.0 points from baseline.

11. The method of claim 1, wherein the dosage form is administered daily for eight weeks or longer, and wherein the patient at week 8 has a mean Y-BOCS total scale change of at least 2.9 points compared to placebo.

12. The method of claim 1, wherein the dosage form is administered daily for twelve weeks or longer, and wherein at week 12 the patient has a mean Y-BOCS total scale change of −7.0 points from baseline.

13. The method of claim 1, wherein the dosage form is administered daily for twelve weeks or longer, and wherein the patient at week 12 has a mean Y-BOCS total scale change of 2.4 points compared to placebo.

14. The method of claim 1, wherein the dosage form comprises troriluzole in an amount of 250 mg or greater.

15. The method of claim 1, wherein the dosage form comprises troriluzole in an amount of 300 mg or greater.

16. The method of claim 1, wherein the dosage form comprises troriluzole in an amount of 350 mg or greater.

17. The method of claim 1, wherein the dosage form comprises troriluzole in an amount of 400 mg or greater.

* * * * *